United States Patent [19]

Braun et al.

[11] 4,331,150
[45] May 25, 1982

[54] APPROXIMATOR FOR ANASTOMOTIC SURGERY

[75] Inventors: Karl Braun, Talheim; Fritz Hilzinger, Emmingen-Liptingen; Erich Wintermantel, Tübingen, all of Fed. Rep. of Germany

[73] Assignee: Aesculap-Werke Aktiengesellschaft Vormals Jetter & Scheerer, Tuttlingen, Fed. Rep. of Germany

[21] Appl. No.: 121,612

[22] Filed: Feb. 14, 1980

[30] Foreign Application Priority Data

Mar. 2, 1979 [DE] Fed. Rep. of Germany ....... 2908209

[51] Int. Cl.³ .............................................. A61B 17/11
[52] U.S. Cl. .............................. 128/334 C; 128/346; 269/45; 269/155
[58] Field of Search ............... 128/346, 325, 321, 322, 128/326, 334 R, 334 C; 24/81 AD; 269/45, 104, 105, 152, 156, 155

[56] References Cited

U.S. PATENT DOCUMENTS

| 783,031 | 2/1905 | Fell | 269/45 |
| 4,165,747 | 8/1979 | Bermant | 128/346 X |

FOREIGN PATENT DOCUMENTS

| 618821 | 4/1961 | Canada | 128/346 |
| 2713093 | 9/1978 | Fed. Rep. of Germany | 128/334 R |

*Primary Examiner*—Michael H. Thaler
*Attorney, Agent, or Firm*—Martin A. Farber

[57] ABSTRACT

An approximator having at least one pair of parallel guide bars which are connected to each other rigidly on one of their adjacent ends, and having at least one clamp of which one is arranged longitudinally displaceable on the guide bars of a pair and is fixable on these in any desired displaced position. At least one additional bar pair each with respectively one displaceable and fixable clamp. The additional bar pair is pivotally connected with the at least one first mentioned bar pair and with respect to this bar pair is fixable in selective relative positions.

6 Claims, 5 Drawing Figures

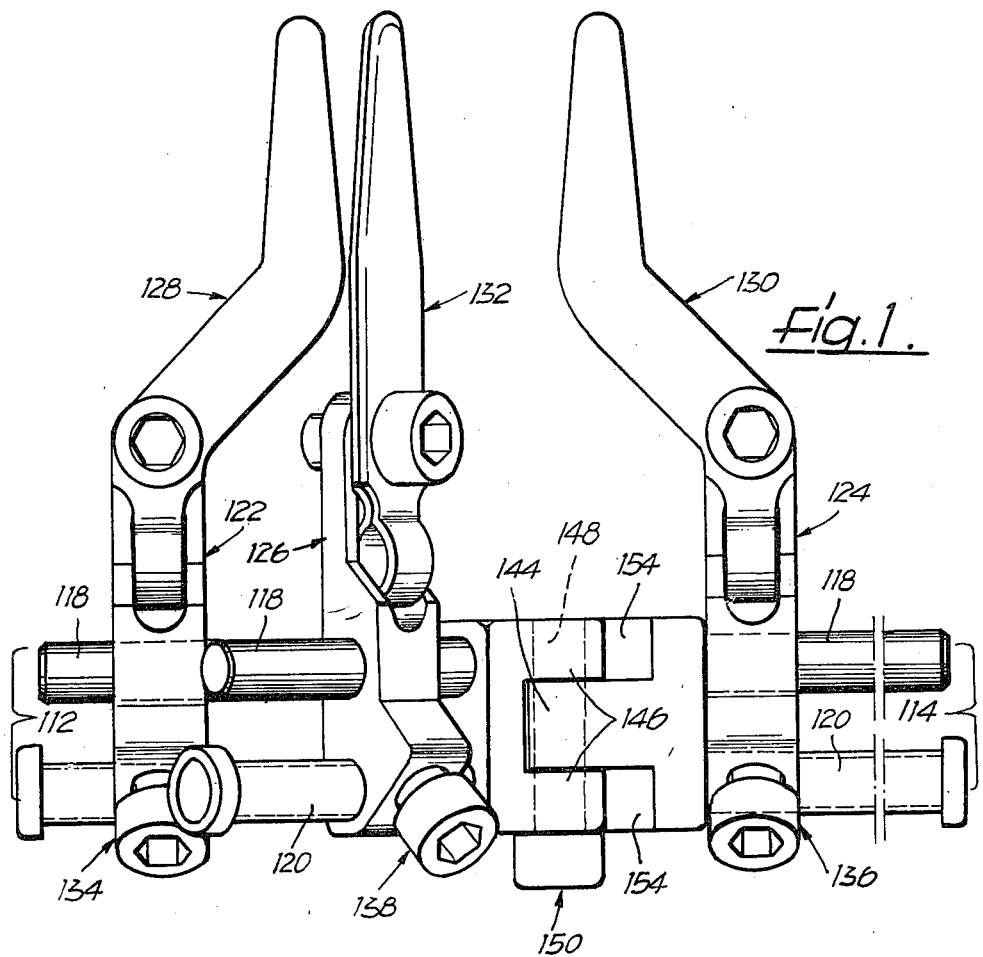
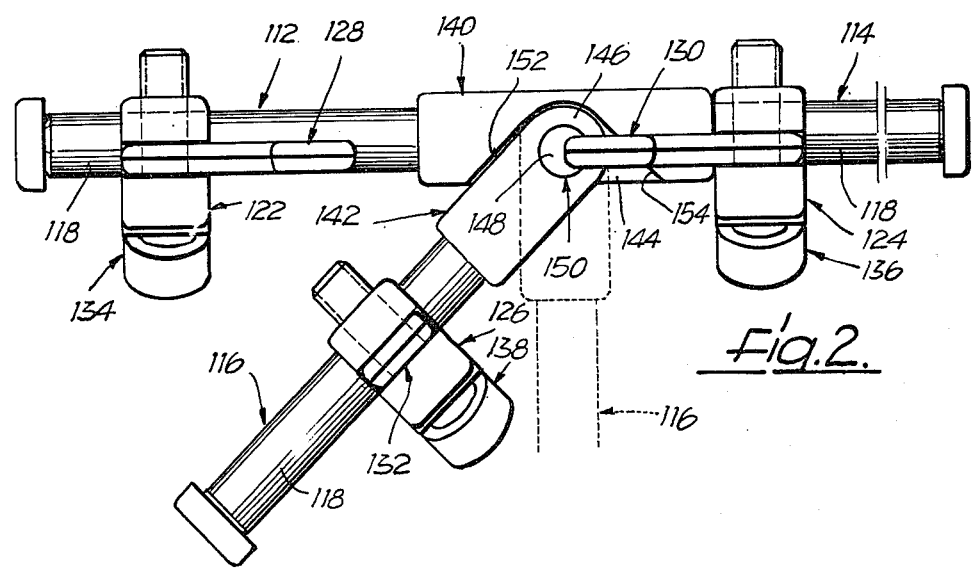

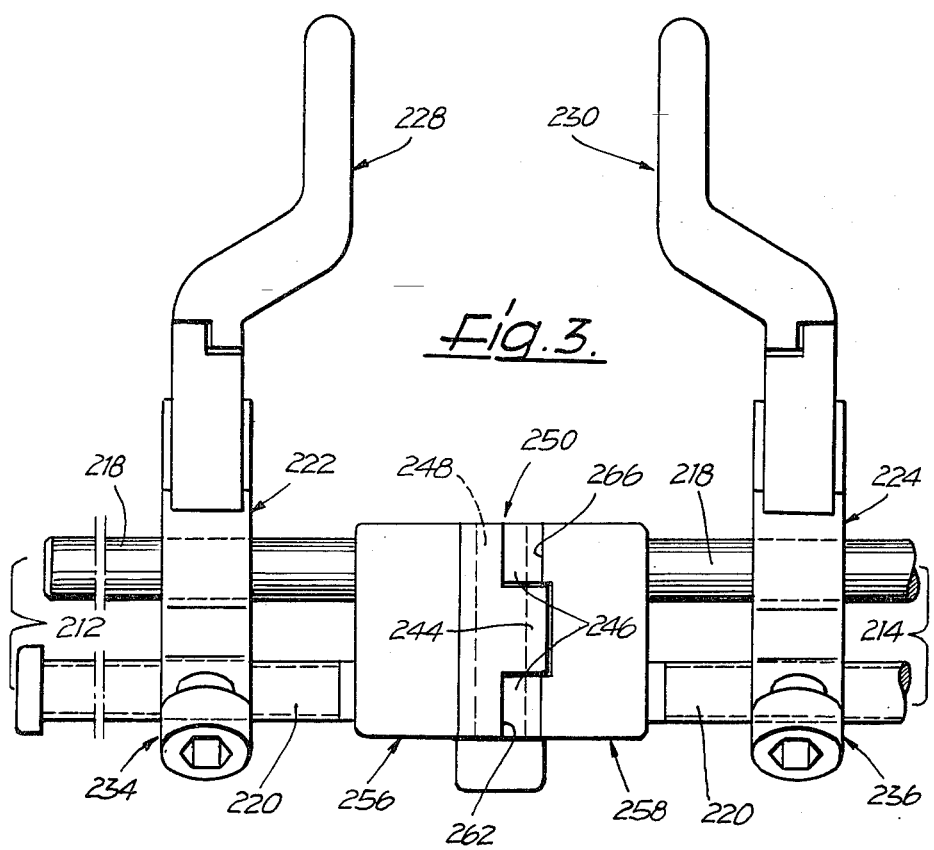
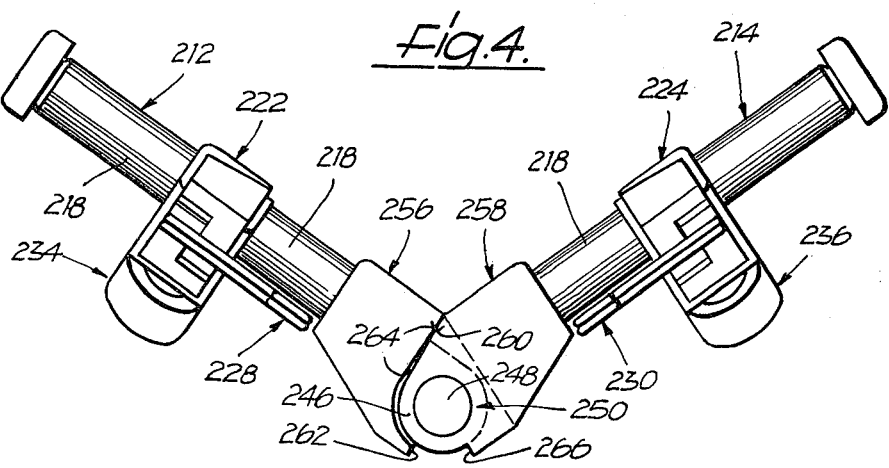

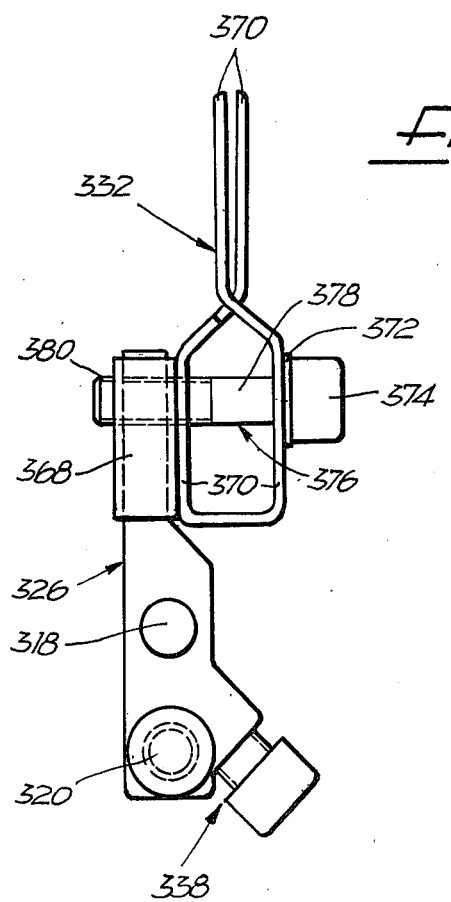

APPROXIMATOR FOR ANASTOMOTIC SURGERY

This invention relates to an approximator having at least one pair of parallel guide bars which are connected to each other rigidly at one of their adjacent ends, and having at least two clamps of which one is arranged longitudinally displaceable on the guide bars of a pair and is fixable on these in any displaced position.

A known approximator of this type is the approximator according to German GS No. 7 632 903 with two parallel guide bars which are rigidly connected with one another by means of a first clamp holder arranged on one end side and by means of a displaceable second clamp holder which is guided on the two bars, with a driving rod similar to a gear rack, which driving rod is arranged parallel to one of the two guide bars and is mounted endsided on the stationary clamp holder and engages through the displaceable clamp holder, with a driver acting on the driving rod, by its rotation about its longitudinal axis the movable clamp holder can be displaced, and with two clamps arranged on their holders, the clamps each having one jaw movable relative to the other.

With this known approximator, the driving rod and the driver are a threaded spindle and a rotary handle fastened to one end of the spindle, respectively. The threaded spindle, with its other end which faces away from the rotary handle, is rotatably mounted on the stationary clamp holder and is threaded through the displaceable clamp holder with which it forms a helical gearing. The driving rod extends centrally through the intermediate space between the two guide bars, parallel to the latter. Accordingly, the turntable handle is located on the end outside of this intermediate space.

The known approximator has the disadvantage that thus neither three vessel-/nerve-ends can be connected with one another nor one vessel-/nerve-end can be connected with one vessel nerve, still two vessel-/nerve-ends with folding together of the two ends which are to be connected during the connection can be connected with one another, particularly during the connection by sewing up.

The object of the present invention therefore is to make an approximator of the introductory mentioned type which avoids this disadvantage and offers one and/or other of the two previously mentioned possibilities.

In accordance with the invention there is provided at least one additional bar pair (116; 214) with each respectively one displaceable and fixable clamp (132, 230), said additional bar pair being pivotally connected with the at least one (remaining) bar pair (112, 114; 212) and with respect to this bar pair (112 or 114; 212) is fixable in selective relative positions. Alternately for realization of the offered possibilities, there are provided three pairs of bars, of which one pair is swingable and fixable, each with one clamp, or two such pairs of bars can be connected with one another pivotally and securely. Further possibilities are open.

U.S. Pat. No. 3,221,743 discloses only a system and a device for the positioning and securing of anastomotic instruments. In this manner never do pairwise occurring pivotally connected guide rods and instruments which can be fixed on them in any spatial position come into use in order for example to hold the opening of an abdominal cover. This known holder mechanism for several or different instruments has hardly any connection with approximators for anastomotic surgery under the microscope.

U.S. Pat. No. 3,035,582 merely discloses an instrument for the holding of tissue by means of several forceps, which instrument indeed has two halves which are pivotally connected with one another, which halves are fixable with respect to one another in selected relative rotary positions. With this however a correspondence with the approximator of the present invention is exhausted.

With a first group of preferred embodiment forms of the approximator according to the invention it is provided that two (112, 114) of three bar pairs (112, 114, 116) with one clamp each are connected rigidly with one another and lie parallel one behind the other. Consequently the basic arrangement of the two clamps of the known approximator is met with the particular advantage that each of the two clamps is displaceable with respect to the other.

With a first embodiment form in this group the third pair (116) of bars is articulated at the connection position of the two others. In this case the new third clamp can approach or can be removed from each of the two other clamps in a certain or predetermined manner so that perpendicular or oblique angle thrusts can be performed without difficulties. Practically it is simplest in this matter that with the first embodiment the two rigidly connected bar pairs (112, 114) are provided wih a common first bar bearing block (140) for their four adjacent bar ends and the pivotally connected bar pair (116) is provided with an individual second bar bearing block (142) for its one ends, the second bearing block being articulated to the first bar bearing block (140).

It is advantageous for the first embodiment that the articulation is brought about by means of a pivot (150), which pivot comprises a joint bar (144) with a bore, which joint bar is formed on the first, or second, bar bearing block (140), comprises a fork (146) formed with two aligned bores, which fork is formed on the second, or respectively, first bar bearing block (142), for the reception of the joint bar and comprises a set screw (148) fitting in the three coaxial bores.

It is of advantage with this embodiment that the first bar bearing block (140) has two abutment surfaces (152, 154) for the movable second bar bearing block (142), which abutment surfaces cooperate with the fork (146), or respectively, with the joint bar. Consequently the pivot range of the third pair of bars is determined with the third clamp.

With a second group of preferred embodiment forms the approximator in accordance with the invention is characterized by two bar pairs (212, 214) with respectively each one clamp (228, 230), which bar pairs are pivotally connected with one another, whereby suitably each bar pair (212, 214) is provided with one own bar bearing block (256, 258) for its two connected bar ends and one bar bearing block (256) is articulated to the other bearing block (258), as above already is proposed for the first embodiment.

With this second embodiment the articulation is executed by means of a pivot (250) which has a joint bar (244) with bore (which joint bar is formed on a bar bearing block (256)) and a fork (246) with aligned bores (which fork is formed on the other bearing block (258)) for reception of the joint bar (244) as well as a set screw (248) fitting in the three coaxial bores, as previously already is correspondingly proposed for the first embodiment form, because such a pivot articulation in a simple way can be precisely produced without play. The allowable tolerances are extremely small with approximators, since with them operations are performed under the microscope.

Similarly as with the first embodiment with the second embodiment each (256) of the two bearing blocks (256, 258) has two abutment surfaces (260, 262), which surfaces cooperate with the abutment surfaces (264, 266) (which are coordinated individually to them) of the respective other bearing block (258).

With a variation of the first embodiment wherein its clamps are constructed as forceps whose tong arms are adjustable with respect to one another by means of a screw, the head of which acts on one of the two tong arms, characterized that the other of the two tong arms (370) is secured on a shoe (368), which shoe is inserted on the clamp holder (326), through which shoe the screw (376) engages in the clamp holder, so that the clamps are securely mounted and are simple to exchange.

With the above and other objects and advantages in view, the present invention will become more clearly understood in connection with the detailed decription of a preferred embodiment, when considered with the accompanying drawings, of which:

FIG. 1 is a side view of the first embodiment of the approximator of the invention;

FIG. 2 is a view of the first embodiment from the top;

FIG. 3 is a side view of the second embodiment;

FIG. 4 is a view of the second embodiment from the top; and

FIG. 5 is a side view of a portion of a modification of the invention.

The first embodiment according to FIGS. 1 and 2 comprises three identical pairs 112, 114 and 116 of parallel bars 118 and 120, three identical clamp holders 122, 124 and 126, three partially (128, 130) alike clamps 128, 130 and 132 as well as three identical shifting devices 134, 136 and 138. With this respectively each one clamp holder, one clamp and one shifting device form a movable unit per bar pair.

The formation of the guide bars, the clamp holder, the clamps and the shifting devices may be gathered from the German GS 7 838 567 (FIGS. 1 and 2) including reference to German GS 7 709 313 (FIGS. 1 to 3) with respect to the formation of the clamps. Also the manner of operation of the shifting devices is explained there.

Each of the clamp holders 122, 124 and 126 with the clamps 128, and respectively 130, and respectively 132, which are arranged on them extends pependicularly to the two planes (the two planes being defined by the three guides bars 118 and 120, respectively) in a cross plane, which cross plane is defined the bars 118 and 120, which guide it, of the associated rod pair. In this manner the sense of direction of the extension is the same. Three vessel-/nerve ends which are fixed by means of the clamps 128, 130 and 132 thus lie in one plane.

In this embodiment example the two clamps 128 and 130 which are opposite one another are angled—or symmetrically shaped such that their free ends always are closer than the corresponding clamp holders 122 and 124.

A first bar bearing block 140 connects the two bar points 112 and 114 and is bridged over by the two angled clamps 128 and 130. By means of two identical or congruent recesses, which are located one over the other, formed in the bearing block 140 is an approximately triangular strip or joint bar 144 which has a bore. The third bar pair 116 is fastened to a second bearing block 142. The bar bearing block 142 is formed with a fork 146 which is formed by means of a center recess. The fork 146 receives the joint bar 144 and has two aligned bores.

A pin the form of a set screw 148 is inserted through the coaxial bores of the strip 144 and of the fork 146. The pivot articulation 150 which is formed from the joint bar 144, the fork 146 and the pin allows the third bar pair 116 with the unit made of the third clamp holder 126, third clamp 132 and the third displacement device 136 to swing about the axis of the pin and thereby to move the clamp 132 on a circular arc with a radius which can be selected by the displacement device 138. The swinging movement is limited by two perpendicular abutment surfaces 152 and 154 of the first bearing block 140 each being on both sides of the joint bar 144, which cooperate with the second bearing block 142. By means of the set screw 148 the selected relative position of the third pair 116 of bars is fixed with respect to the two others.

The axis of the pin=screw 148 is naturally arranged so that it intersects the parallel axes of the third bar pair 116 and lies in a plane, which plane is perpendicular to the plane which is defined in common by the two bar pairs 112 and 114, as well as run parallel to the common plane.

Parts of the second embodiment according to FIGS. 3 and 4 which correspond to the first embodiment are designated with the same reference numbers as in the previous embodiments but raised by the number 100.

The second embodiment is characterized by the two individual, angled clamps 228 and 230 of the type of construction described in German GS 7 709 313 (FIGS. 4 to 7) and by the absence of the third bar pair with the unit made of the third clamp holder, third clamp and third displaceable device. The second embodiment corresponds with the first embodiment in that one bar bearing block 256 and another bar bearing block 258 are connected to one another by means of a pivot 250 which is formed corresponding to the pivot of the first embodiment. Abutment surfaces 260 and 262 on one bearing block 256 are arranged for cooperation with abutment surfaces 264 and 266 on the other bar bearing block 258. These abutment surfaces limit the two angles between which the bar pair 212 which is fixed on the bearing block 256 can swing with respect to the second bar pair 214 which is fixed on the other bearing block 258 and vice versa. If the abutment surfaces 262 and 266 which are spaced apart from one another with the angled approximator are guided together and mutually contact, the approximator is extended, that is the four axes of the guide bars 218 and 220 of the two bar pairs 212 and 214 lie in one and the same plane.

By means of the screw 248 serving again as a pivot pin the two bar pairs 212 and 214 are fixable in any selected relative position.

With a variation according to FIG. 5 of the first embodiment form according to FIG. 1 (center) a shoe 368 is inserted on each or any of the three clamp carriers (326). On the shoe, one of the two crossed spring tong arms 370 of a crossing clamps (332) is laterally rigidly fastened. The head 374 of a screw 376 acts on the other spring tong arm 370 via a soft washer 372. The shaft 378 of the screw 374 is inserted through the sections of the two tong arms 370 which follow in parallel at the backs 380 of the crossing forceps (332) and is inserted through the shoe 368 and is screwed by means of an outer threading 382 in the clamp holder (326). By turning of the screw head 374 in one direction, or a direction opposite thereto, the two tong arms 370 open and respectively close the cross clamps (332) at their free ends which are spaced from the backs. Therefore a preliminary adjustment of the crossing clamps is possible. Moreover parts of this variation which are the same as the first embodiment are denoted with the same reference numerals but raised by 200 numbers.

While we have disclosed several embodiments of the invention it is to be understood that these embodiments are given by example only and not in a limiting sense.

We claim:

1. An approximator, comprising
   two guide bar pairs each comprising parallel guide bars connected to each other rigidly on one of their adjacent ends, respectively,
   at least one clamp being disposed on each of said two guide bar pairs, at least one of said at least one clamp being mounted longitudinally displaceable on each of said two guide bar pairs and fixable thereon in any displaced position,
   a third guide bar pair comprising parallel guide bars,
   at least one additional clamp being mounted longitudinally displaceably and fixably on said third guide bar pair,
   means for pivotally connecting said third guide bar pair with said two guide bar pairs and for fixing said third guide bar pair in selective relative positions with respect to said two guide bars pairs,
   said two guide bar pairs are rigidly connected with one another at a connection point and are disposed parallel one behind the other, corresponding of said guide bars of each of said guide bar pairs are oriented in one plane, respectively, the respective planes of different of said corresponding guide bars of each of said guide bar pairs being parallel to each other in all said relative positions,
   said means being for articulating said third guide bar pair at said connection point of said two guide bar pairs,
   said clamps are constructed as forceps each having two tong arms,
   screw means for adjusting said tong arms with respect to each other, said screw means has a head operatively acting on one of said two tong arms,
   at least one of said clamps includes a clamp holder means for mounting said at least one of said clamps on a corresponding of said guide bar pairs, and
   said pivotally connecting means constitutes a unitary combined means for pivotally connecting and fixedly stabilizing said guide bar pairs in the selective relative positions connected to said guide bar pairs at a single pivot point thereof.

2. The approximator according to claim 1, wherein said pivotally connected means comprises,
   a common first bar bearing block is connected to said two guide bar pairs at four adjacent ends of said parallel guide bars,
   an individual second bar bearing block, one adjacent ends of said third guide bar pair are disposed in said second bar bearing block, said second bar bearing block being articulated to said first bar bearing block.

3. The approximator according to claim 2, wherein said pivotally connected means includes,
   a pivot comprising,
   a joint bar formed with a bore, said joint bar is formed on one of said bar bearing blocks,
   a fork formed with two coaxially aligned bores, said fork is formed on the other of said bearing blocks, said joint bar is disposed in said fork such that said two coaxially aligned bores are coaxial to said first-mentioned bore, and
   a set screw fitting in the three coaxial bores.

4. The approximator according to claim 3, wherein said second bar bearing block constitutes a moveable bar bearing block,
   said first bar bearing block includes means constituting two abutment surfaces for abutment with said movable bearing block,
   said abutment surfaces cooperate with said fork.

5. The approximator according to claim 3, wherein said second bar bearing block constitutes a moveable bar bearing block,
   said first bar bearing block includes means constituting two abutment surfaces for abutment with said movable bearing block,
   said abutment surfaces cooperate with said joint bar.

6. An approximator according to claim 1, further comprising
   a shoe inserted on said clamp holder means,
   the other of said two tong arms is secured on said shoe,
   said screw means extends through said shoe and engages in said clamp holder means.

* * * * *